United States Patent [19]

Elbe et al.

[11] Patent Number: 5,789,437
[45] Date of Patent: Aug. 4, 1998

[54] MICROBICIDAL COMPOSITIONS BASED ON DIBROMO-THIOPHENE-CARBOXYLIC ACID DERIVATIVES

[75] Inventors: Hans-Ludwig Elbe, Wuppertal; Lutz Assmann, Eutin; Ralf Tiemann, Leverkusen; Uta Ecker, Leichlingen; Gerd Hänssler, Leverkusen; Heinz-Wilhelm Dehne, Bonn, all of Germany

[73] Assignee: Bayer Aktiengesellschaft, Leverkusen, Germany

[21] Appl. No.: 722,262

[22] PCT Filed: Mar. 29, 1995

[86] PCT No.: PCT/EP95/01173

§ 371 Date: Oct. 4, 1996

§ 102(e) Date: Oct. 4, 1996

[87] PCT Pub. No.: WO95/27397

PCT Pub. Date: Oct. 19, 1995

[30] Foreign Application Priority Data

Apr. 11, 1994 [DE] Germany .................. 44 12 333.7

[51] Int. Cl.⁶ .................. A01N 43/06; C07D 333/38; C07D 333/22
[52] U.S. Cl. .................. 514/448; 549/71; 549/72; 549/73
[58] Field of Search .................. 514/448; 549/71, 549/72, 73

[56] References Cited

U.S. PATENT DOCUMENTS 3,536,473  10/1970  Popoff et al. .................. 549/71
5,034,049   7/1991  Kober et al. .................. 549/72

*Primary Examiner*—Deborah C. Lambkin
*Attorney, Agent, or Firm*—Sprung Kramer Schaefer & Briscoe

[57] ABSTRACT

New microbicidal compositions based on dibromo-thiophene-carboxylic acid derivatives which are known in some cases, of the formula

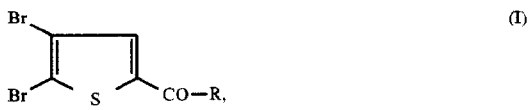

in which R represents the groups $-XR^1$, $-NR^2R^3$, $-NR^4OR^5$ or $-NR^4-N(R^5)_2$, where X represents oxygen or sulphur and $R^1$, $R^2$, $R^3$, $R^4$ and $R^5$ have the meanings indicated in the description, and the use of these substances for controlling undesired microorganisms.

New dibromo-thiophene-carboxylic acid derivatives of the formula

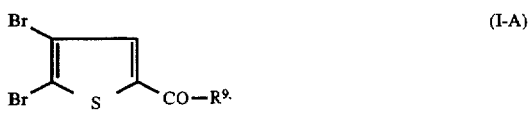

in which $R^9$ represents the groups $-SR^1$, $-OR^{10}$,

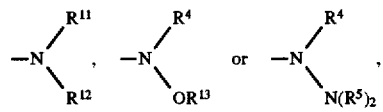

in which $R^1$, $R^4$, $R^5$, $R^{10}$, $R^{11}$, $R^{12}$ and $R^{13}$ have the meaning indicated in the description, and processes for the preparation of the substances of the formula (I-A).

7 Claims, No Drawings

MICROBICIDAL COMPOSITIONS BASED ON DIBROMO-THIOPHENE-CARBOXYLIC ACID DERIVATIVES

This application is a 371 of PCT/EP95/01173 Mar. 29, 1995.

The present invention relates to novel microbicidal compositions based on dibromothiophene-carboxylic acid derivatives which are known in some cases, and the use of these substances for controlling undesired microorganisms. Additionally, the invention also relates to new dibromo-thiophene-carboxylic acid derivatives and a plurality of processes for their preparation.

It has already been disclosed that certain halogenothiophene-carboxamide derivatives can be employed for controlling plant diseases (cf. EP-OS 0 450 355). The activity of these previously known compounds, however, is not completely satisfactory in all fields of application, in particular at low application rates.

Furthermore, certain 4,5-dibromo-thiophene-2-carboxylic acid derivatives are known, such as, for example, the compounds 4,5-dibromo-thiophene-2-carboxylic acid methyl ester (CA Reg. No. 62224-24-2) and ethyl ester (CA Reg. No. 62224-25-3) and 1,1-dimethylethyl ester (CA Reg. No. 62224-26-4) and 2-propinyl ester (CA Reg. No. 116 041-66-8) and 1-methyl-2-propinyl ester (CA Reg. No. 131 818-24-1) and 3-butinyl ester (CA Reg. No. 131 818-21-8) and N,N-dimethylamide (CA Reg. No. 111 859-96-2) and N-ethoxy-amide (CA Reg. No. 131 818-25-2) and also 4,5-dibromothiophene-2-carboxylic acid (CA Reg. No. 6324-10-3) and -carboxamide (Beilstein Reg. No. 129 357).

To date, nothing is known about fungicidal activity of these compounds.

It has now been found that the dibromo-thiophene-carboxylic acid derivatives, which are known in some cases, of the formula

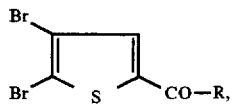

(I)

in which

R represents the groups —$XR^1$, —$NR^2R^3$, —$NR^4OR^5$ or —$NR^4$—$N(R^5)_2$, where X represents oxygen or sulphur, $R^1$ represents hydrogen, or straight-chain or branched alkyl which can be substituted by halogen, cyano, amino, hydroxyl, mercapto, carboxyl, nitro, alkoxy, alkylthio, alkoxycarbonyl and/or the group

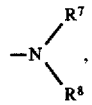

or $R^1$ represents optionally substituted alkenyl or optionally substituted alkinyl, or $R^1$ represents cycloalkyl or cycloalkylalkyl, each of which is optionally substituted, tetrahydrofuran, tetrahydrothiophene, tetrahydropyran or tetrahydrothiopyran, each of which is optionally substituted, and aryl, aralkyl, hetaryl or hetarylalkyl, each of which is optionally substituted, $R^2$ and $R^3$ are identical or different and represent hydrogen, or alkyl which can be substituted by halogen, cyano, amino, hydroxyl, mercapto, nitro, alkoxy, alkylthio and/or the group

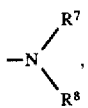

or represent alkenyl which is optionally substituted by halogen, or alkinyl which is optionally substituted by halogen, or represent cycloalkyl or cycloalkylalkyl, where each of these radicals can be substituted by alkyl, halogen, halogenoalkyl, cyano, alkylenedioxo, cycloalkyl which is optionally substituted by alkyl, and/or by optionally substituted phenyl, or represent tetrahydrofuran, tetrahydrothiophene, tetrahydropyran or tetrahydrothiopyran, each of which is optionally substituted, and optionally substituted aralkyloxy, $R^3$ additionally represents hetaryl or hetarylalkyl, each of which is optionally substituted, $R^2$ and $R^3$ furthermore together represent divalent alkanediyl, it being possible for a $CH_2$ group to be replaced by O, S or $NR^6$, $R^4$ and $R^5$ are identical or different and represent hydrogen; alkyl, alkenyl or alkinyl, each of which is optionally substituted; and optionally substituted aralkyl, $R^6$ represents hydrogen, alkyl or alkylcarbonyl, $R^7$ represents optionally substituted alkyl, optionally substituted alkenyl, optionally substituted alkinyl or optionally substituted benzyl and $R^8$ represents hydrogen, optionally substituted alkyl, optionally substituted alkenyl, optionally substituted alkinyl or optionally substituted benzyl, or $R^7$ and $R^8$ together represent divalent alkanediyl, it being possible for a $CH_2$ group to be replaced by O, S or $NR^6$, where $R^6$ has the meanings indicated above, are very highly suitable for controlling undesired microorganisms.

Depending on the nature of the substituents, the compounds of the formula (I) can exist as geometric and/or optical isomers or isomer mixtures of differing composition. The invention relates both to the use of the pure isomers and of the isomer mixtures.

Formula (I) provides a general definition of the dibromo-thiophene-carboxylic acid derivatives which can be used according to the invention.

R preferably represents the groups —$XR^1$, —$NR^2R^3$, —$NR^4OR^5$ and —$NR^4$—$N(R^5)_2$.

X preferably represents oxygen or sulphur.

$R^1$ preferably represents hydrogen, or straight-chain or branched alkyl having 1 to 12 carbon atoms, which can be mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or represents straight-chain or branched alkenyl and alkinyl having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned can be mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms which is optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, which is optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aryl having 6 to 10 carbon atoms or aralkyl having 6 to 10 carbon atoms in the aryl moiety and 1 to 4 carbon atoms in the straight-chain or branched alkyl moiety, which is optionally substituted by cyano, where each of the two radicals in the aryl moiety can be mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl which for its part can be mono- to trisubstituted, identically or differently, by halogen and/or alkyl having 1 to 4 carbon atoms, or 5- or 6-membered hetaryl or 5- or 6-membered hetarylalkyl having 1 to 6 carbon atoms in the straight-chain or branched alkyl moiety, which is optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms.

$R^2$ and $R^3$ are identical or different and preferably represent hydrogen, or straight-chain or branched alkyl having 1 to 12 carbon atoms, which can be mono- to pentasubstituted, identically or differently, by halogen, cyano, amino, hydroxyl, mercapto, nitro, straight-chain or branched alkoxy having 1 to 6 carbon atoms, straight-chain or branched alkylthio having 1 to 6 carbon atoms and/or the group

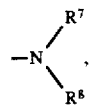

or straight-chain or branched alkenyl or alkinyl having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned can be mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aralkoxy having 6 or 10 carbon atoms in the aryl moiety and 1 to 4 carbon atoms in the straight-chain or branched alkoxy moiety, optionally substituted by cyano, where the aryl moiety can be mono- to trisubstituted, identically or differently, by halogen, hydroxyl, cyano, nitro; alkyl, alkoxy or alkylthio, each of which is straight-chain or branched each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl, which for its part can be mono- to trisubstituted, identically or differently, by halogen and/or alkyl having 1 to 4 carbon atoms.

$R^3$ additionally preferably represents 5- or 6-membered hetaryl or 5- or 6-membered hetarylalkyl having 1 to 6 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms.

$R^2$ and $R^3$ additionally together preferably represent divalent alkanediyl having 2 to 6 $CH_2$ groups, where a $CH_2$ group is optionally replaced by O, S or $NR^6$.

$R^4$ and $R^5$ are identical or different and preferably represent hydrogen, or straight-chain or branched alkyl having 1 to 12 carbon atoms, which can be mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or straight-chain or branched alkenyl and alkinyl having 3 to 6 carbon atoms, each of which is optionally mono- to pentasubstituted, identically or differently, by halogen, or aralkyl having 6 or 10 carbon atoms in the aryl moiety and 1 to 4 carbon atoms in the straight-chain or branched alkyl moiety, optionally substituted by cyano, where the aryl moiety can be mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or difcanent halogen atoms; and/or by phenyl, which for its part can be mono- to trisubstituted, identically or differently, by halogen and/or alkyl having 1 to 4 carbon atoms.

$R^6$ preferably represents hydrogen, and also alkyl and alkylcarbonyl, each of which is straight-chain or branched, each having 1 to 6 carbon atoms in the alkyl moiety.

$R^7$ preferably represents straight-chain or branched alkyl having 1 to 6 carbon atoms, which can be mono- to pentasubstituted, identically or differently, by halogen, cyano, amino, hydroxyl, mercapto, nitro, carboxyl; alkoxy and alkoxycarbonyl, each of which is straight-chain or branched, each having 1 to 6 carbon atoms in the alkoxy moieties; alkylamino and dialkylamino having 1 to 6 carbon atoms in each straight-chain or branched alkyl moiety, or straight-chain or branched alkenyl or alkinyl each having 3 to 6 carbon atoms, each of which is optionally substituted by 1 to 5 identical or different halogen atoms, or benzyl which in the phenyl moiety can be mono- to trisubstituted, identically or differently, by halogen, nitro, cyano, straight-chain or branched alkyl having 1 to 6 carbon atoms, and also halogenoalkyl, halogenoalkoxy or halogenoalkylthio, each of which is straight-chain or branched, each having 1 to 4 carbon atoms and 1 to 5 identical or different halogen atoms.

$R^8$ preferably represents hydrogen, or straight-chain or branched alkyl having 1 to 6 carbon atoms, which can be mono- to pentasubstituted, identically or differently, by halogen, cyano, amino, hydroxyl, mercapto, nitro, carboxyl; alkoxy and alkoxycarbonyl, each of which is straight-chain or branched, each having 1 to 6 carbon atoms in the alkoxy moieties, alkylamino and dialkylamino having 1 to 6 carbon atoms in each straight-chain or branched alkyl moiety, or straight-chain or branched alkenyl or alkinyl each having 3 to 6 carbon atoms, each of which is optionally substituted by 1 to 5 identical or different halogen atoms, or benzyl which in the phenyl moiety can be mono- to trisubstituted, identically or differently, by halogen, nitro, cyano, straight-chain or branched alkyl having 1 to 6 carbon atoms, and also halogenoalkyl, halogenoalkoxy or halogenoalkylthio, each of which is straight-chain or branched, each having 1 to 4 carbon atoms and 1 to 5 identical or different halogen atoms.

$R^7$ and $R^8$ additionally together preferably represent divalent alkanediyl having 4 to 6 $CH_2$ groups, it optionally being possible for a $CH_2$ group to be replaced by O, S or $NR^6$ and $R^6$ having the meanings mentioned as preferred above.

R particularly preferably represents the groups —$XR^1$, —$NR^2R^3$, —$NR^4OR^5$ and —$NR^4$—$N(R^5)_2$.

X particularly preferably represents oxygen or sulphur.

$R^1$ particularly preferably represents hydrogen, or straight-chain or branched alkyl having 1 to 8 carbon atoms, which can be mono- to tetrasubstituted, identically or differently, by fluorine, chlorine, cyano, amino, hydroxyl, mercapto; alkoxy and alkylthio, each of which is straight-chain or branched, each having 1 to 6 carbon atoms; and also the group —$NR^7R^8$, or straight-chain or branched alkenyl or alkinyl having 3 to 6 carbon atoms, each of which is optionally mono- to trisubstituted, identically or differently, by fluorine, chlorine and/or bromine, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, optionally substituted by cyano, where the cycloalkyl moiety of the two radicals mentioned can be mono- to tetrasubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms, cyclohexyl or cyclopentyl, optionally substituted by methyl or ethyl, and/or by phenyl which for its part can be mono- or disubstituted, identically or differently, by methyl, ethyl, fluorine, chlorine and/or halogenoalkyl having 1 or 2 carbon atoms and 1 to 3 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms, cyclohexyl or cyclopentyl, optionally substituted by methyl or ethyl, and/or by phenyl, which for its part can be mono- or disubstituted, identically or differently, by methyl, ethyl, fluorine, chlorine and/or halogenoalkyl having 1 or 2 carbon atoms and 1 to 3 identical or different halogen atoms, or phenyl, naphthyl, phenylalkyl or naphthylalkyl having 1 to 4 carbon atoms in the straight-chain or branched alkyl moiety, optionally substituted by cyano, where each of the four radicals mentioned can be mono- to trisubstituted in the aryl moiety, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 2 carbon atoms and 1 to 5 identical or different halogen atoms; and/or phenyl which is optionally mono- to trisubstituted, identically or differently, by halogen and/or alkyl having 1 to 2 carbon atoms, or 5- or 6-membered hetaryl or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 4 carbon atoms, fluorine, chlorine, bromine, cyano and halogenoalkyl having 1 to 2 carbon atoms and 1 to 5 identical or different halogen atoms.

$R^2$ and $R^3$ are identical or different and particularly preferably represent hydrogen, or straight-chain or branched alkyl having 1 to 8 carbon atoms, which can be mono- to tetrasubstituted, identically or differently, by fluorine, chlorine, cyano, amino, hydroxyl, mercapto; alkoxy and alkylthio, each of which is straight-chain or branched, each having 1 to 6 carbon atoms; and the group —$NR^7R^8$, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, optionally substituted by cyano, where the cycloalkyl moiety of the two radicals mentioned can be mono- to tetrasubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms, cyclohexyl or cyclopentyl, optionally substituted by methyl or ethyl, and/or by phenyl, which for its part can be mono- or disubstituted, identically or differently, by methyl, ethyl, fluorine, chlorine and/or halogenoalkyl having 1 or 2 carbon atoms and 1 to 3 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms, cyclohexyl or cyclopentyl, optionally substituted by methyl or ethyl, and/or by phenyl, which for its part can be mono- or disubstituted, identically or differently, by methyl, ethyl, fluorine, chlorine and/or halogenoalkyl having 1 or 2 carbon atoms and 1 to 3 identical or different halogen atoms, or phenylalkoxy or naphthylalkoxy having 1 to 4 carbon atoms in the straight-chain or branched alkyl moiety, optionally substituted by cyano, where each of these radicals mentioned can be mono- to trisubstituted in the aryl moiety, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 2 carbon atoms and 1 to 5 identical or different halogen atoms and/or phenyl which is optionally mono- to trisubstituted, identically or differently, by halogen and/or alkyl having 1 to 2 carbon atoms.

$R^3$ additionally particularly preferably represents 5- or 6-membered hetaryl or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 4 carbon atoms, fluorine, chlorine, bromine, cyano and halogenoalkyl having 1 to 2 carbon atoms and 1 to 5 identical or different halogen atoms.

$R^2$ and $R^3$ additionally together particularly preferably represent divalent alkanediyl having 4 to 6 $CH_2$ groups, it optionally being possible for a $CH_2$ group to be replaced by O, S or $NR^6$.

$R^4$ and $R^5$ are identical or different and particularly preferably represent hydrogen, or straight-chain or branched alkyl having 1 to 8 carbon atoms, which can be mono- to tetrasubstituted, identically or differently, by fluorine, chlorine, cyano, amino, hydroxyl, mercapto; alkoxy and alkylthio, each of which is straight-chain or branched, each having 1 to 6 carbon atoms; and the group —$NR^7R^8$, straight-chain or branched alkenyl or alkinyl having 3 to 6 carbon atoms, each of which is optionally mono- to trisubstituted, identically or differently, by fluorine, chlorine and/or bromine, or phenylalkyl or naphthylalkyl having 1 to 4 carbon atoms in the straight-chain or branched alkyl moiety, optionally substituted by cyano, where each of the four radicals mentioned can be mono- to trisubstituted in the aryl moiety, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 2 carbon atoms and 1 to 5 identical or different halogen atoms; and/or phenyl which is optionally mono- to trisubstituted, identically or differently, by halogen and/or alkyl having 1 to 2 carbon atoms.

$R^6$ particularly preferably represents hydrogen, and also alkyl and alkylcarbonyl, each of which is straight-chain or branched, each having 1 to 4 carbon atoms in the alkyl moiety.

$R^7$ particularly preferably represents straight-chain or branched alkyl having 1 to 6 carbon atoms, which can be mono- to tetrasubstituted, identically or differently, by fluorine, chlorine, cyano, amino, hydroxyl, carboxyl; and also alkoxy and alkoxycarbonyl, each of which is straight-chain or branched, each having 1 to 4 carbon atoms in the alkoxy moieties; or straight-chain or branched alkenyl having 3 to 6 carbon atoms, optionally substituted by 1 to 3 halogen atoms, straight-chain or branched alkinyl having 3 to 6 carbon atoms, or benzyl which can be mono- to trisubstituted in the phenyl moiety, identically or differently, by fluorine, chlorine and/or straight-chain or branched alkyl having 1 to 4 carbon atoms.

$R^8$ particularly preferably represents hydrogen, or straight-chain or branched alkyl having 1 to 6 carbon atoms, which can be mono- to tetrasubstituted, identically or differently, by fluorine, chlorine, cyano, amino, hydroxyl, carboxyl; and also alkoxy and alkoxycarbonyl, each of which is straight-chain or branched, each having 1 to 4 carbon atoms in the alkoxy moieties, or straight-chain or branched alkenyl having 3 to 6 carbon atoms, optionally substituted by 1 to 3 halogen atoms, straight-chain or branched alkinyl having 3 to 6 carbon atoms, or benzyl which can be mono- to trisubstituted in the phenyl moiety, identically or differently, by fluorine, chlorine and/or straight-chain or branched alkyl having 1 to 4 carbon atoms.

$R^7$ and $R^8$ additionally together particularly preferably represent divalent alkanediyl having 4 to 6 $CH_2$ groups, it optionally being possible for a $CH_2$ group to be replaced by O, S or $NR^6$ and $R^6$ having the meanings mentioned above as particularly preferred.

R very particularly preferably represents the groups $-XR^1$, $-NR^2R^3$, $-NR^4OR^5$ and $-NR^4-N(R^5)_2$.

X very particularly preferably represents oxygen or sulphur.

$R^1$ very particularly preferably represents hydrogen, or methyl, ethyl, n- or i-propyl, n-, i-, s- or t-butyl, n- or i-pentyl, n- or i-hexyl, n- or i-heptyl and n- or i-octyl, where each of these radicals can be mono- to trisubstituted, identically or differently, by fluorine, chlorine, cyano, amino, hydroxyl, mercapto, methoxy, ethoxy, n- or i-propoxy, n-, i-, s- or t-butoxy, methylthio, ethylthio, n- or i-propylthio or the group $-NR^7R^8$, or allyl, n- or i-butenyl, n- or i-pentenyl, n- or i-hexenyl, propargyl, n- or i-butinyl, n- or i-pentinyl and n- or i-hexinyl, each of which is optionally mono- to trisubstituted, identically or differently, by fluorine and/or chlorine, or cyclopropyl, cyclopropylmethyl, cyclopropylethyl, cyclopropylpropyl, cyclopropyl-1-cyanoeth-1-yl, cyclopropyl-cyanomethyl,cyclopentyl, cyclopentylmethyl, cyclopentylethyl, cyclopentylpropyl, cyclopentyl-cyanomethyl, cyclopentyl-1-cyanoeth-1-yl, cyclohexyl, cyclohexylmethyl, cyclohexylethyl, cyclohexylpropyl, cyclohexyl-cyanomethyl, cyclohexyl-1-cyanoeth-1-yl, cycloheptyl, cycloheptylmethyl, cycloheptylethyl, cycloheptylpropyl, cycloheptyl-cyanomethyl or cycloheptyl-1-cyanoeth-1-yl, each of which is optionally mono- to tetrasubstituted in the cycloalkyl moiety, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or tetrahydrofuran, tetrahydrothiophene, tetrahydropyran or tetrahydrothiopyran, where each of these radicals can be mono- to trisubstituted, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or phenyl, naphthyl, phenylalkyl or naphthylalkyl having 1 to 4 carbon atoms in the straight-chain or branched alkyl moiety, optionally substituted by cyano, where each of these radicals can be mono- to trisubstituted in the aryl moiety, identically or differently, by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio or phenyl which is optionally mono- to trisubstituted, identically or differently, by fluorine, chlorine, bromine, methyl and/or ethyl, or 5- or 6-membered hetaryl, or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by methyl, ethyl, n- or i-propyl, n-, i-, s- or t-butyl, fluorine, chlorine, bromine, cyano, trifluoromethyl, difluoromethyl, chlorodifluoromethyl, bromodifluoromethyl, chloromethyl or dichloromethyl.

$R^2$ and $R^3$ are identical or different and very particularly preferably represent hydrogen, or methyl, ethyl, n- or i-propyl, n-, i-, s- or t-butyl, n- or i-pentyl, n- or i-hexyl, n- or i-heptyl and n- or i-octyl, where each of these radicals can be mono- to trisubstituted, identically or differently, by fluorine, chlorine, cyano, amino, hydroxyl, mercapto, methoxy, ethoxy, n- or i-propoxy, n-, i-, s- or t-butoxy, methylthio, ethylthio, n- or i-propylthio or the group $-NR^7R^8$, or allyl, n- or i-butenyl, n- or i-pentenyl, n- or i-hexenyl, propargyl, n- or i-butinyl, n- or i-pentinyl and n- or i-hexinyl, each of which is optionally mono- to trisubstituted, identically or differently, by fluorine and/or chlorine, or cyclopropyl, cyclopropylmethyl, cyclopropylethyl, cyclopropylpropyl, cyclopropyl-1-cyanoeth-1-yl, cyclopropyl-cyanomethyl, cyclopentyl, cyclopentylmethyl, cyclopentylethyl, cyclopentylpropyl, cyclopentyl-cyanomethyl, cyclopentyl-1-cyanoeth-1-yl, cyclohexyl, cyclohexylmethyl, cyclohexylethyl, cyclohexylpropyl, cyclohexyl-cyanomethyl, cyclohexyl-1-cyanoeth-1-yl, cycloheptyl, cycloheptylmethyl, cycloheptylethyl, cycloheptylpropyl, cycloheptyl-cyanomethyl or cycloheptyl-1-cyanoeth-1-yl, each of which is optionally mono- to tetrasubstituted in the cycloalkyl moiety, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or tetrahydrofuran, tetrahydrothiophene, tetrahydropyran or tetrahydrothiopyran, where each of these radicals can be mono- to trisubstituted, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or phenylalkoxy or naphthylalkoxy having 1 to 4 carbon atoms in the straight-chain or branched, optionally [lacuna] by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio or phenyl which is optionally mono- to trisubstituted, identically or differently, by fluorine, chlorine, bromine, methyl and/or ethyl.

$R^3$ additionally very particularly preferably represents 5- or 6-membered hetaryl, or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by methyl, ethyl, n- or i-propyl, n-, i-, s- or t-butyl, fluorine, chlorine, bromine, cyano, trifluoromethyl, difluoromethyl, chlorodifluoromethyl, bromodifluoromethyl, chloromethyl or dichloromethyl.

$R^2$ and $R^3$ additionally together very particularly preferably represent divalent alkanediyl having 4 or 5 $CH_2$ groups, it optionally being possible for a $CH_2$ group to be replaced by O, S or $NR^6$.

$R^4$ and $R^5$ are identical or different and very particularly preferably represent hydrogen, or methyl, ethyl, n- or i-propyl, n-, i-, s- or t-butyl, n- or i-pentyl, n- or i-hexyl, n- or i-heptyl and n- or i-octyl, where each of these radicals can be mono- to trisubstituted, identically or differently, by fluorine, chlorine, cyano, amino, hydroxyl, mercapto, methoxy, ethoxy, n- or i-propoxy, n-, i-, s- or t-butoxy, methylthio, ethylthio, n- or i-propylthio or the group —$NR^7R^8$, or allyl, n- or i-butenyl, n- or i-pentenyl, n- or i-hexenyl, propargyl, n- or i-butinyl, n- or pentinyl and n- or i-hexinyl, each of which is optionally mono- to trisubstituted, identically or differently, by fluorine and/or chlorine, or phenylalkyl or naphthylalkyl having 1 to 4 carbon atoms in the straight-chain or branched alkyl moiety, optionally substituted by cyano, where each of the two radicals mentioned can be mono- to trisubstituted in the aryl moiety, identically or differently, by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio or phenyl which is optionally mono- to trisubstituted, identically or differently, by fluorine, chlorine, bromine, methyl and/or ethyl.

$R^6$ very particularly preferably represents hydrogen, methyl, ethyl, n- or i-propyl, n-, i-, s- or t-butyl, acetyl, ethylcarbonyl, n- or i-propylcarbonyl or n-, i-, s- or t-butylcarbonyl.

$R^7$ very particularly preferably represents methyl, ethyl, n- or i-propyl, n-, i-, s- or t-butyl, n- or i-pentyl and n- or i-hexyl, where each of these radicals can be mono- to trisubstituted, identically or differently, by cyano, amino, hydroxyl, carboxyl, methoxy, ethoxy, n- or i-propoxy, n-, i-, s- or t-butoxy, acetyl, ethylcarbonyl, n- or i-propylcarbonyl and n-, i-, s- or t-butylcarbonyl, or allyl, n- or i-butenyl, n- or i-pentenyl and n- or i-hexenyl, each of which is optionally mono- to trisubstituted, identically or differently, by fluorine and/or chlorine, or propargyl, n- or i-butinyl, n- or i-pentinyl and n- or i-hexinyl, or benzyl which can be mono- to trisubstituted in the phenyl moiety, identically or differently, by fluorine, chlorine, bromine, methyl, ethyl, n- or i-propyl and n-, i-, s- or t-butyl.

$R^8$ very particularly preferably represents hydrogen, or methyl, ethyl, n- or i-propyl, n-, i-, s- or t-butyl, n- or i-pentyl and n- or i-hexyl, where each of these radicals can be mono- to trisubstituted, identically or differently, by cyano, amino, hydroxyl, carboxyl, methoxy, ethoxy, n- or i-propoxy, n-, i-, s- or t-butoxy, acetyl, ethylcarbonyl, n- or i-propylcarbonyl and n-, i-, s- or t-butylcarbonyl, or allyl, n- or i-butenyl, n- or i-pentenyl and n- or i-hexenyl, each of which is optionally mono- to trisubstituted, identically or differently, by fluorine and/or chlorine, or propargyl, n- or i-butinyl, n- or i-pentinyl and n- or i-hexinyl, or benzyl which can be mono- to trisubstituted in the phenyl moiety, identically or differently, by fluorine, chlorine, bromine, methyl, ethyl, n- or i-propyl and n-, i-, s- or t-butyl.

$R^7$ and $R^8$ additionally very particularly preferably represent divalent alkanediyl having 4 or 5 $CH_2$ groups, it optionally being possible for a $CH_2$ group to be replaced by O, S or $NR^6$ and $R^6$ having the meanings mentioned above as very particularly preferred.

The dibromo-thiophene-carboxylic acid derivatives of the formula (I) which can be used according to the invention are known in some cases (cf. Chem. Ber. 18(1885), 2312; DE-OS [German Published Specification] 39 01 074; U.S. Pat. No. 3,536,473 EP 0 258 790 JP-OS [Japanese Published Specification] 62-138, 489 and J. Chem. Soc. Perkin Trans. 1 (1973) 1766, 1772, 1773).

New dibromo-thiophene-carboxylic acid derivatives are those of the formula

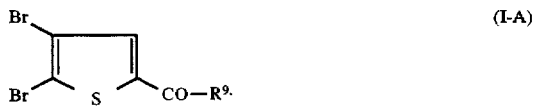

(I-A)

in which $R^9$ represents the groups $-SR^1$, $-OR^{10}$,

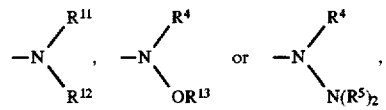

$R^1$ represents hydrogen or straight-chain or branched alkyl which can be substituted by halogen, cyano, amino, hydroxyl, mercapto, carboxyl, nitro, alkoxy, alkylthio, alkoxycarbonyl and/or the group

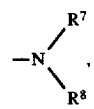

or $R^1$ represents optionally substituted alkenyl or optionally substituted alkinyl, or $R^1$ represents cycloalkyl or cycloalkylalkyl, each of which is optionally substituted, tetrahydrofuran, tetrahydrothiophene, tetrahydropyran or tetrahydrothiopyran, each of which is optionally substituted, or aryl, aralkyl, hetaryl or hetarylalkyl, each of which is optionally substituted, $R^{10}$ represents straight-chain or branched alkyl which is substituted by halogen, cyano, amino, hydroxyl, mercapto, carboxyl, nitro, alkoxy, alkylthio, alkoxycarbonyl and/or the group

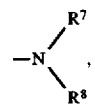

or $R^{10}$ represents optionally substituted alkenyl or substituted alkinyl, or $R^{10}$ represents cycloalkyl or cycloalkylalkyl, each of which is optionally substituted, tetrahydrofuran, tetrahydrothiophene, tetrahydropyran or tetrahydrothiopyran, each of which is optionally substituted, or aryl, aralkyl, hetaryl or hetarylalkyl, each of which is optionally substituted, $R^{11}$ and $R^{12}$ are identical or different and represent alkyl which is substituted by halogen, cyano, amino, hydroxyl, mercapto, nitro, alkoxy, alkylthio and/or the group

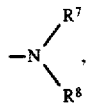

or alkenyl which is optionally substituted by halogen or alkinyl which is optionally substituted by halogen, or cycloalkyl or cycloalkylalkyl, where each of these radicals can be substituted by alkyl, halogen, halogenoalkyl, cyano, alkylenedioxo, cycloalkyl which is optionally substituted by alkyl, and/or by optionally substituted phenyl, or tetrahydrofuran, tetrahydrothiophene, tetrahydropyran or tetrahydrothiopyran, each of which is optionally substituted, or optionally substituted aralkoxy, $R^{12}$ additionally represents hetaryl or hetarylalkyl, each of which is optionally substituted, $R^{11}$ and $R^{12}$ furthermore together represent divalent alkanediyl, where a $CH_2$ group can be replaced by O, S or $NR^6$, $R^4$ and $R^5$ are identical or different and represent hydrogen; alkyl, alkenyl or alkinyl, each of which is optionally substituted; or optionally substituted aralkyl, $R^6$ represents hydrogen, alkyl or alkylcarbonyl, $R^7$ represents optionally substituted alkyl, optionally substituted alkenyl, optionally substituted alkinyl or optionally substituted benzyl and $R^8$ represents hydrogen, optionally substituted alkyl, optionally substituted alkyl, optionally substituted alkenyl, optionally substituted alkinyl or optionally substituted benzyl, or $R^7$ and $R^8$ together represent divalent alkanediyl, it being possible for a $CH_2$ group to be replaced by O, S or $NR^6$, where $R^6$ has the meanings indicated above and $R^{13}$ represents hydrogen, substituted alkyl, optionally substituted alkenyl, optionally substituted alkinyl or optionally substituted aralkyl.

Dibromo-thiophene-carboxylic acid derivatives of the formula (I-A) can be prepared by reacting dibromo-thiophene-carbonyl halides of the formula

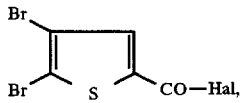

(II)

in which

Hal represents halogen, either a) with amines of the formula

H—$R^{14}$, (III)

in which $R^{14}$ represents the groups

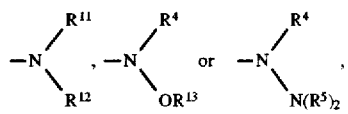

in which $R^4$, $R^5$, $R^{11}$, $R^{12}$ and $R^{13}$ have the meanings indicated above, if appropriate in the presence of a diluent and if appropriate in the presence of a reaction auxiliary, or b) with alcohols or thioalcohols of the formulae $$HO—R^{10} \qquad (IV)$$

or $$HS—R^1, \qquad (VI)$$

in which $R^1$ and $R^{10}$ have the meaning indicated above, if appropriate in the presence of a diluent and if appropriate in the presence of a reaction auxiliary, and if appropriate in the presence of a catalyst.

The already-known dibromo-thiophene-carboxylic acid derivatives of the formula (I) can be prepared analogously.

Formula (I-A) provides a general definition of the new dibromo-thiophene-carboxylic acid derivatives.

$R^9$ preferably represents the groups —$SR^1$, —$OR^{10}$,

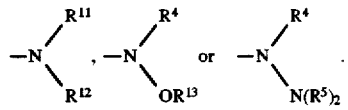

In connection with the definitions of the substituents of the formula (I-A), $R^1$, $R^4$, $R^5$, $R^6$, $R^7$ and $R^8$ preferably represent those meanings which have already been mentioned above as preferred.

$R^{10}$ preferably represents straight-chain or branched alkyl, having 1 to 12 carbon atoms, which can be mono- to pentasubstituted, identically or differently, by halogen, cyano, amino, hydroxyl, mercapto, carboxyl, nitro; alkoxy, alkylthio or alkoxycarbonyl, each of which is straight-chain or branched, in each case having 1 to 6 carbon atoms in the individual alkyl moieties; and also the group —$NR^7R^8$, or straight-chain or branched alkenyl and alkinyl, each having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety which is optionally substituted by cyano, where the cycloalkyl moiety of the two radicals mentioned can be mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms which is optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms which is optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aryl having 6 to 10 carbon atoms or aralkyl having 6 to 10 carbon atoms in the aryl moiety and 1 to 4 carbon atoms in the straight-chain or branched alkyl moiety, which is optionally substituted by cyano, where each of the two radicals in the aryl moiety can be mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms, and/or by phenyl which for its part can be mono- to trisubstituted, identically or differently, by halogen and/or alkyl having 1 to 4 carbon atoms, or 5- or 6-membered hetaryl or 5- or 6-membered hetarylalkyl having 1 to 6 carbon atoms in the straight-chain or branched alkyl moiety, which is optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms.

$R^{11}$ and $R^{12}$ are identical or different and preferably represent straight-chain or branched alkyl having 1 to 12 carbon atoms, which can be mono- to pentasubstituted, identically or differently, by halogen, cyano, amino, hydroxyl, mercapto, nitro, straight-chain or branched alkoxy having 1 to 6 carbon atoms, straight-chain or branched alkylthio having 1 to 6 carbon atoms and/or the group

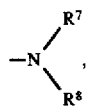

or straight-chain or branched alkenyl or alkinyl having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned can be mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aralkoxy having 6 or 10 carbon atoms in the aryl moiety and 1 to 4 carbon atoms in the straight-chain or branched alkoxy moiety, optionally substituted by cyano, where the aryl moiety can be mono- to trisubstituted, identically or differently, by halogen, hydroxyl, cyano, nitro; alkyl, alkoxy or alkylthio in each case having 1 to 4 carbon atoms, each of which is straight-chain or branched; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms, and/or by phenyl, which for its part can be mono- to trisubstituted, identically or differently, by halogen and/or alkyl having 1 to 4 carbon atoms.

$R^{12}$ additionally preferably represents 5- or 6-membered hetaryl or 5- or 6-membered hetarylalkyl having 1 to 6 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms.

$R^{11}$ and $R^{12}$ additionally together preferably represent divalent alkanediyl having 2 to 6 $CH_2$ groups, where a $CH_2$ group is optionally replaced by O, S or $NR^6$.

$R^{13}$ preferably represents hydrogen, or straight-chain or branched alkyl having 1 to 12 carbon atoms, which is mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group $—NR^7R^8$, or straight-chain or branched alkenyl and alkinyl having 3 to 6 carbon atoms, each of which is optionally mono- to pentasubstituted, identically or differently, by halogen, or aralkyl having 6 or 10 carbon atoms in the aryl moiety and 1 to 4 carbon atoms in the straight-chain or branched alkyl moiety, optionally substituted by cyano, where the aryl moiety can be mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl, which for its part can be mono- to trisubstituted, identically or differently, by halogen and/or alkyl having 1 to 4 carbon atoms.

$R^9$ particularly preferably represents the groups $—SR^1$, $—OR^{10}$,

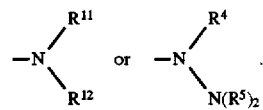

In connection with the definitions of the substituents of the formula (I-A), $R^1$, $R^4$, $R^5$, $R^6$, $R^7$ and $R^8$ particularly preferably represent those meanings which have already been mentioned above as particularly preferred.

$R^{10}$ particularly preferably represents straight-chain or branched alkyl having 1 to 8 carbon atoms, which can be mono- to tetrasubstituted, identically or differently, by fluorine, chlorine, cyano, amino, hydroxyl, mercapto, alkoxy and alkylthio, each of which is straight-chain or branched, each having 1 to 6 carbon atoms, and the group $—NR^7R^8$, or straight-chain or branched alkenyl having 3 to 6 carbon atoms, optionally mono- to trisubstituted, identically or differently, by fluorine, chlorine and/or bromine, or straight-chain or branched alkinyl having 3 to 6 carbon atoms, mono- to trisubstituted, identically or differently, by fluorine, chlorine and/or bromine, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, optionally substituted by cyano, where the cycloalkyl moiety of the two radicals mentioned can be mono- to tetrasubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms; cyclohexyl or cyclopentyl, each of which is optionally substituted by methyl or ethyl; and/or by phenyl which for its part can be mono- or disubstituted, identically or differently, by methyl, ethyl, fluorine, chlorine and/or halogenoalkyl having 1 or 2 carbon atoms and 1 to 3 identical or different halogen atoms, or phenyl, naphthyl, phenylalkyl or naphthylalkyl having 1 to 4 carbon atoms in the straight-chain or branched alkyl moiety, optionally substituted by cyano, where each of the four radicals mentioned can be mono- to trisubstituted in the aryl moiety, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 2 carbon atoms and 1 to 5 identical or different halogen atoms; and/or phenyl which is optionally mono- to trisubstituted, identically or differently, by halogen and/or alkyl having 1 to 2 carbon atoms, or 5- or 6-membered hetaryl or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 4 carbon atoms, fluorine, chlorine, bromine, cyano and halogenoalkyl having 1 to 2 carbon atoms and 1 to 5 identical or different halogen atoms.

$R^{11}$ and $R^{12}$ are identical or different and particularly preferably represent straight-chain or branched alkyl having 1 to 8 carbon atoms, which can be mono- to tetrasubstituted, identically or differently, by fluorine, chlorine, cyano, amino, hydroxyl, mercapto; alkoxy and alkylthio, each of which is straight-chain or branched, each having 1 to 6 carbon atoms; and the group —$NR^7R^8$, or straight-chain or branched alkenyl or alkinyl having 3 to 6 carbon atoms, in each case optionally mono- to trisubstituted, identically or differently, by fluorine, chlorine and/or bromine, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, optionally substituted by cyano, where the cycloalkyl moiety of the two radicals mentioned can be mono- to tetrasubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms; cyclohexyl or cyclopentyl, each of which is optionally substituted by methyl or ethyl; and/or by phenyl, which for its part can be mono- or disubstituted, identically or differently, by methyl, ethyl, fluorine, chlorine and/or halogenoalkyl having 1 or 2 carbon atoms and 1 to 3 identical or different halogen atoms, or tetrahydrofuran, tetrahydrothiophene, tetrahydropyran or tetrahydrothiopyran, where each of these radicals can be mono- to trisubstituted, identically or differently, by straight-chain or branched alkyl having 1 to 4 carbon atoms, halogen, straight-chain or branched halogenoalkyl having 1 to 4 carbon atoms and 1 to 3 identical or different halogen atoms, cyano, alkylenedioxo having 1 or 2 carbon atoms; cyclohexyl or cyclopentyl, each of which is optionally substituted by methyl or ethyl; and/or by phenyl, which for its part can be mono- or disubstituted, identically or differently, by methyl, ethyl, fluorine, chlorine and/or halogenoalkyl having 1 or 2 carbon atoms and 1 to 3 identical or different halogen atoms, or phenylalkoxy or naphthylalkoxy having 1 to 4 carbon atoms in the straight-chain or branched alkyl moiety, optionally substituted by cyano, where each of these radicals mentioned can be mono- to trisubstituted in the aryl moiety, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 2 carbon atoms and 1 to 5 identical or different halogen atoms; and/or phenyl which is optionally mono- to trisubstituted, identically or differently, by halogen and/or alkyl having 1 to 2 carbon atoms.

$R^{12}$ additionally particularly preferably represents 5- or 6-membered hetaryl or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by straight-chain or branched alkyl having 1 to 4 carbon atoms, fluorine, chlorine, bromine, cyano and halogenoalkyl having 1 to 2 carbon atoms and 1 to 5 identical or different halogen atoms.

$R^{11}$ and $R^{12}$ additionally together particularly preferably represent divalent alkanediyl having 4 to 6 $CH_2$ groups, it optionally being possible for a $CH_2$ group to be replaced by O, S or $NR^6$.

$R^{13}$ particularly preferably represents hydrogen, or straight-chain or branched alkyl having 1 to 8 carbon atoms, which can be mono- to tetrasubstituted, identically or differently, by fluorine, chlorine, cyano, amino, hydroxyl, mercapto; alkoxy and alkylthio, each of which is straight-chain or branched, each having 1 to 6 carbon atoms; and the group —$NR^7R^8$, or straight-chain or branched alkenyl or alkinyl having 3 to 6 carbon atoms, each of which is optionally mono- to trisubstituted, identically or differently, by fluorine, chlorine and/or bromine, or phenylalkyl or naphthylalkyl having 1 to 4 carbon atoms in the straight-chain or branched alkyl moiety, optionally substituted by cyano, where each of the two radicals mentioned can be mono- to trisubstituted in the aryl moiety, identically or differently, by halogen, hydroxyl, cyano, nitro; alkyl, alkoxy or alkylthio, each of which is straight-chain or branched, each having 1 to 4 carbon atoms, cycloalkyl having 3 to 7 carbon atoms; halogenoalkyl, halogenoalkoxy or halogenoalkylthio, each of which is straight-chain or branched, each having 1 or 2 carbon atoms and 1 to 5 identical or different halogen atoms; and/or phenyl which is optionally mono- to trisubstituted, identically or differently, by halogen and/or alkyl having 1 or 2 carbon atoms.

$R^9$ very particularly preferably represents the groups —$SR^1$, —$OR^{10}$.

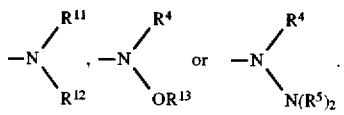

In connection with the definitions of the substituents of the formula (I-A), $R^1$, $R^4$, $R^5$, $R^6$, $R^7$ and $R^8$ very particularly preferably represent those meanings which have already been mentioned above as very particularly preferred.

$R^{10}$ very particularly preferably represents methyl, ethyl, n- or i-propyl, n-, i-, s- or t-butyl, n- or i-pentyl, n- or i-hexyl, n- or i-heptyl and n- or i-octyl, where each of these radicals can be mono- to trisubstituted, identically or differently, by fluorine, chlorine, cyano, amino, hydroxyl, mercapto, methoxy, ethoxy, n- or i-propoxy, n-, i-, s- or t-butoxy, methylthio, ethylthio, n- or i-propylthio or the group —NR$^7$R$^8$, or allyl, n- or i-butenyl, n- or i-pentenyl, n- or i-hexenyl, each of which is optionally mono- to trisubstituted, identically or differently, by fluorine and/or chlorine, or propargyl, n- or i-butinyl, n- or i-pentinyl and n- or i-hexinyl, each of which is optionally mono- to trisubstituted, identically or differently, by fluorine and/or chlorine, or cyclopropyl, cyclopropylmethyl, cyclopropylethyl, cyclopropylpropyl, cyclopropyl-1-cyanoeth-1-yl, cyclopropyl-cyanomethyl,cyclopentyl, cyclopentylmethyl, cyclopentylethyl, cyclopentylpropyl, cyclopentyl-cyanomethyl, cyclopentyl-1-cyanoeth-1-yl, cyclohexyl, cyclohexylmethyl, cyclohexylethyl, cyclohexylpropyl, cyclohexyl-cyanomethyl, cyclohexyl-1-cyanoeth-1-yl, cycloheptyl, cycloheptylmethyl, cycloheptylethyl, cycloheptylpropyl, cycloheptyl-cyanomethyl or cycloheptyl-1-cyanoeth-1-yl, each of which is optionally mono- to tetrasubstituted in the cycloalkyl moiety, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or tetrahydrofuran, tetrahydrothiophene, tetrahydropyran or tetrahydrothiopyran, where each of these radicals can be mono- to trisubstituted, identically or differently, by methyl, ethyl, n- or i-propyl, fluoro, chloro, bromo, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or phenyl, naphthyl, phe-nylalkyl or naphthylalkyl having 1 to 4 carbon atoms in the straight-chain or branched alkyl moiety, optionally substituted by cyano, where each of these radicals can be mono- to trisubstituted in the aryl moiety, identically or differently, by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio or phenyl which is optionally mono- to trisubstituted, identically or differently, by fluorine, chlorine, bromine, methyl and/or ethyl, or 5- or 6-membered hetaryl or 5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by methyl, ethyl, n- or i-propyl, n-, i-, s- or t-butyl, fluorine, chlorine, bromine, cyano, trifluoromethyl, difluoromethyl, chlorodifluoromethyl, bromodifluoromethyl, chloromethyl or dichloromethyl.

$R^{11}$ and $R^{12}$ are identical or different and very particularly preferably represent methyl, ethyl, n- or i-propyl, n-, i-, s- or t-butyl, n- or i-pentyl, n- or i-hexyl, n- or i-heptyl and n- or i-octyl, where each of these radicals is mono- to trisubstituted, identically or differently, by fluorine, chlorine, cyano, amino, hydroxyl, mercapto, methoxy, ethoxy, n- or i-propoxy, n-, i-, s- or t-butoxy, methylthio, ethylthio, n- or i-propylthio or the group —NR$^7$R$^8$, or allyl, n- or i-butenyl, n- or i-pentenyl, n- or i-hexenyl, propargyl, n- or i-butinyl, n- or i-pentinyl and n- or i-hexinyl, each of which is optionally mono- to trisubstituted, identically or differently, by fluorine and/or chlorine, or cyclopropyl, cyclopropylmethyl, cyclopropylethyl, cyclopropylpropyl, cyclopropyl-1-cyanoeth-1-yl, cyclopropyl-cyanomethyl, cyclopentyl, cyclopentylmethyl, cyclopentylethyl, cyclopentylpropyl, cyclopentyl-cyanomethyl, cyclopentyl-1-cyanoeth-1-yl, cyclohexyl, cyclohexylmethyl, cyclohexylethyl, cyclohexylpropyl, cyclohexyl-cyanomethyl, cyclohexyl-1-cyanoeth-1-yl, cycloheptyl, cycloheptylmethyl, cycloheptylethyl, cycloheptylpropyl, cycloheptyl-cyanomethyl or cycloheptyl-1-cyanoeth-1-yl, each of which is optionally mono- to tetrasubstituted in the cycloalkyl moiety, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or tetrahydrofuran, tetrahydrothiophene, tetrahydropyran or tetrahydrothiopyran, where each of these radicals can be mono- to trisubstituted, identically or differently, by methyl, ethyl, n- or i-propyl, fluorine, chlorine, bromine, trifluoromethyl, difluoromethyl, chlorodifluoromethyl, bromodifluoromethyl, chloromethyl, dichloromethyl, cyano, methylenedioxo, ethylenedioxo, methylcyclopentyl, methylcyclohexyl, ethylcyclopentyl, ethylcyclohexyl, phenyl, chlorophenyl, dichlorophenyl, fluorophenyl, difluorophenyl, chlorofluorophenyl, methylphenyl, dimethylphenyl, chloromethylphenyl, fluoromethylphenyl, trifluoromethylphenyl, chloro-trifluoromethylphenyl or fluoro-trifluoromethyl, or phenylalkoxy or naphthylalkoxy having 1 to 4 carbon atoms in the straight-chain or branched alkyl moiety, optionally substituted by cyano, where each of these radicals mentioned can be mono- to trisubstituted in the aryl moiety, identically or differently, by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio or phenyl which is optionally mono- to trisubstituted, identically or differently, by fluorine, chlorine, bromine, methyl and/or ethyl.

$R^{12}$ additionally very particularly preferably represents
5- or 6-membered hetaryl or
5- or 6-membered hetarylalkyl having 1 to 4 carbon atoms in the straight-chain or branched alkyl moiety, optionally substituted by cyano, where the hetaryl moiety in each case contains 1 to 3 heteroatoms, such as oxygen, sulphur and/or nitrogen, and can be mono- to trisubstituted, identically or differently, by methyl, ethyl, n- or i-propyl, n-, i-, s- or t-butyl, fluorine, chlorine, bromine, cyano, trifluoromethyl, difluoromethyl, chlorodifluoromethyl, bromodifluoromethyl, chloromethyl or dichloromethyl.

$R^{11}$ and $R^{12}$ additionally together very particularly preferably represent divalent alkanediyl having 4 or 5 $CH_2$ groups, it optionally being possible for a $CH_2$ group to be replaced by O, S or $NR^6$.

$R^{13}$ very particularly preferably represents hydrogen, or methyl, ethyl, n- or i-propyl, n-, i-, s- or t-butyl, n- or i-pentyl, n- or i-hexyl, n- or i-heptyl and n- or i-octyl, where each of these radicals can be mono- to trisubstituted, identically or differently, by fluorine, chlorine, cyano, amino, hydroxyl, mercapto, methoxy, ethoxy, n- or i-propoxy, n-, i-, s- or t-butoxy, methylthio, ethylthio, n- or i-propylthio or the group —$NR^7R^8$, or
allyl, n- or i-butenyl, n- or i-pentenyl, n- or i-hexenyl, propargyl, n- or i-butinyl, n- or i-pentinyl and n- or i-hexinyl, each of which is optionally mono- to trisubstituted, identically or differently, by fluorine and/or chlorine, or
phenylalkyl or naphthylalkyl having 1 to 4 carbon atoms in the straight-chain or branched alkyl moiety, optionally substituted by cyano, where each of the two radicals mentioned can be mono- to trisubstituted in the aryl moiety, identically or differently, by fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio or phenyl which is optionally mono- to trisubstituted, identically or differently, by fluorine, chlorine, bromine, methyl and/or ethyl.

If, for example, 4,5-dibromo-thiophene-2-carbonyl chloride and benzyloxyamine are used as starting substances, the course of the reaction of process (a) according to the invention can be represented by the following equation:

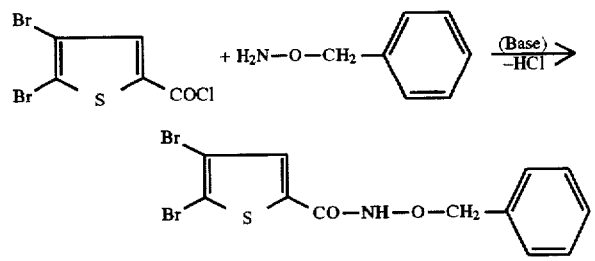

If, for example, 4,5-dibromo-thiophene-2-carbonyl bromide and cyclohexanol are used as starting substances, the course of the reaction of process (b) according to the invention can be represented by the following equation:

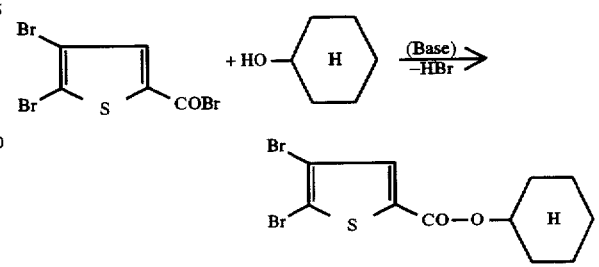

Formula (II) provides a general definition of the dibromo-thiophene-carbonyl halides needed as starting substances for carrying out processes (a) and (b) according to the invention. In this formula (II), Hal is preferably chlorine or bromine.

The dibromo-thiophene-carbonyl halides of the formula (II) are known (cf., for example, EP-OS [European Published Specification] 0 450 355; U.S. Pat. No. 3,303,201; DE-OS [German Published Specification] 12 01 952; GB-PS 1085 974).

Formula (III) provides a general definition of the amines furthermore needed as starting substances for carrying out process (a) according to the invention. In this formula (III), $R^{14}$ preferably represents the groups —$NR^{11}R^{12}$, —$NR^4OR^{13}$ and —$NR^4$—$N(R^5)_2$, where $R^4$, $R^5$, $R^{11}$, $R^{12}$ and $R^{13}$ preferably represent those radicals which have already been mentioned as preferred for these substituents in connection with the description of the compounds of the formulae (I) and (I-A) which can be used according to the invention.

The amines of the formula (III) are generally known compounds of organic chemistry or are obtainable in analogy to generally known processes.

Formulae (IV) and (V) provide a general definition of the alcohols and thioalcohols furthermore needed as starting substances for carrying out process (b) according to the invention. In these formulae (IV) and (V), $R^1$ and $R^{10}$ preferably represent those radicals which have already been mentioned as preferred for these substituents in connection with the description of the compounds of the formulae (I) and (I-A) which can be used according to the invention.

The alcohols of the formula (IV) and the thioalcohols of the formula (V) are generally known compounds of organic chemistry or are obtainable in analogy to generally known processes.

Possible diluents for carrying out process (a) according to the invention are inert organic solvents. Those which can preferably be used are aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoramide; esters such as methyl acetate or ethyl acetate or sulphoxides, such as dimethyl sulphoxide.

Process (a) according to the invention is preferably carried out in the presence of a suitable reaction auxiliary. Those which are suitable are all customary inorganic or organic bases. Those which can preferably be used are alkaline earth metal or alkali metal hydrides, hydroxides, amides, alkoxides, acetates, carbonates or hydrogen carbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogen carbonate, sodium hydrogen carbonate, and further ammonium hydroxide, ammonium acetate or ammonium carbonate as well as tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

Process (a) according to the invention can optionally also be carried out in a two-phase system, such as, for example, water/toluene or water/dichloromethane, if appropriate in the presence of a suitable phase-transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyldimethyl-ammonium methylsulphate, dimethyl-$C_{12}$/$C_{14}$-alkyl-benzylammonium chloride, dimethyl-$C_{12}$/$C_{14}$-alkyl-benzyl-ammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

When carrying out process (a) according to the invention, the reaction temperatures can be varied within a relatively wide range. In general, the reaction is carried out at temperatures between $-20°$ C. and $150°$ C., preferably at temperatures between $0°$ C. and $120°$ C.

Process (a) according to the invention is customarily carried out under normal pressure. However, it is also possible to work at elevated or reduced pressure.

To carry out process (a) according to the invention, in general 1.0 to 5.0 mol, preferably 1.0 to 2.5 mol, of amine of the formula (III) and optionally 1.0 to 5.0 mol, preferably 1.0 to 2.5 mol, of base used as reaction auxiliary are employed per mole of dibromo-thiophene-carbonyl halide of the formula (II). The reaction is carried out and worked up and the reaction products are isolated according to generally known processes (cf. for this also the Preparation Examples).

Suitable diluents for carrying out process (b) according to the invention are inert organic solvents. Those which can preferably be used are aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; nitriles, such as acetonitrile, propionitrile or benzonitrile; amides, such as N,N-dimethylformamide, N,N-dimethylacetamide, N-methylformanilide, N-methylpyrrolidone or hexamethylphosphoramide or sulphoxides, such as dimethyl sulphoxide.

Process (b) according to the invention is preferably carried out in the presence of a suitable reaction auxiliary. Those which are suitable are all customary inorganic or organic bases. Those which can preferably be used are alkaline earth metal or alkali metal hydrides, hydroxides, amides, alkoxides, acetates, carbonates or hydrogen carbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium hydrogen carbonate, sodium hydrogen carbonate, and further ammonium hydroxide, ammonium acetate or ammonium carbonate as well as tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

Process (b) according to the invention is additionally optionally carried out in the presence of a suitable catalyst. Those which are suitable are in particular copper(I) salts, such as, for example, copper(I) chloride. In this connection, the addition of catalytic amounts of a suitable phase-transfer catalyst, such as, for example, 15-crown-5, 18-crown-6 or tris-[2-(2-methoxyethoxy)-ethyl]-amine, can be advantageous.

When carrying out process (b) according to the invention, the reaction temperatures can be varied within a relatively wide range. In general, the reaction is carried out at temperatures between $-20°$ C. and $+180°$ C., preferably at temperatures between $0°$ C. and $+150°$ C.

Process (b) according to the invention is customarily carried out under normal pressure. However, it is also possible to work at elevated or reduced pressure.

To carry out process (b) according to the invention, in general 1.0 to 3.0 mol, preferably 1.0 to 1.5 mol, of alcohol of the formula (IV) or thioalcohol of the formula (V) and optionally 0.1 to 3.0 mol, preferably 0.5 to 1.5 mol, of base used as reaction auxiliary are employed per mole of dibromo-thiophene-carbonyl halide of the formula (II). The reaction is carried out and worked up, and the reaction products are in each case isolated according to generally known processes (cf. for this also the Preparation Examples).

Purification of the final products of the formula (I) is carried out with the aid of customary processes, for example by column chromatography or by recrystallization.

Characterization is carried out with the aid of the melting point or, in the case of non-crystallizing compounds, with the aid of the refractive index or of proton nuclear magnetic resonance spectroscopy ($^1$H-NMR).

The active compounds of the formula (I), according to the invention, have a potent action against microorganisms and can be employed in practice for controlling undesired microorganisms. The active compounds are particularly suitable for use as fungicides and resistance inducers.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;
Phytophthora species, such as, for example, *Pseudoperonospora humuli* or *Pseudoperonospora cubensis*;
Plasmopara species, such as, for example, *Plasmopara viticola*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechlera, syn: Helminthosporium);
Uromyces species, such as, for example, *Uromyces appendiculatus*;
Puccinia species, such as, for example, *Puccinia recondita*;
Tilletia species, such as, for example, *Tilletia caries*;
Ustilago species, such as, for example, *Ustilago nuda* or *Ustilago avenae*;
Pellucularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae*;
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed here to particularly good effect for controlling diseases in fruit- and vegetable-growing, such as, for example, against the causative organism of late blight of tomato (Phytophthora infestans) or against the causative organism of apple scab (Venturia inaequalis) or against the causative organism of powdery mildew on grapevines (Uncinula necator) or against the causative organism of rust on beans (Uromyces appendiculatus) or for controlling rice diseases, such as, for example, against the causative organism of rice blast disease (Pyricularia oryzae) or for controlling powdery mildew fungi on cereals, apples and cucumbers and also for controlling *Alternaria solani* and *Peronospora brassicae*.

The active compounds according to the invention additionally have a strong resistance-inducing action in plants. They are therefore suitable for producing resistance in plants to attack by undesired microorganisms.

Resistant-inducing substances are understood in the present context as meaning those substances which on the one hand, when acting directly on the undesired microorganisms, only exhibit a low activity, but are able to stimulate the defence system of plants such that the treated plants, when subsequently inoculated with undesired microorganisms, display extensive resistance to these microorganisms.

Undesired microorganisms are to be understood in the present case as meaning phytophatogenic fungi, bacteria and viruses. The substances according to the invention can thus be employed in order to produce resistance in plants within a certain period of time after treatment to attack by the harmful causative organisms mentioned. The period of time within which resistance is produced in general extends from 1 to 10 days, preferably 1 to 7 days, after the treatment of the plants with the active compounds.

The undesired microorganisms in plant protection include fungi from the classes of the Plasmodiophoromycetes, Oomycetes, Chytridiomycetes, Zygomycetes, Ascomycetes, Basidiomycetes and Deuteromycetes.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho-lipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper cobalt, molybdenum and zinc.

The formulations in general contain between 0.1 and 95 per cent by weight of active compound, preferably between 0.5 and 90%.

The active compounds according to the invention, as such or in their formulations can also be used as a mixture with known fingicides, bactericides, acaricides, nematicides or insecticides, for example to widen the spectrum of action or to prevent the build-up of resistance. In many cases, synergistic effects are obtained, i.e. the activity of the mixture is greater than the activity of the individual components.

Examples of particularly advantageous mixtures are the following compounds.

Fungicides 2-aminobutane; 2-anilino-4-methyl-6-cyclopropyl-pyrimidine;2', 6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]-phenyl}-3-methoxyacrylate; methyl (E)-methoximino[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, proparnocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations Insecticides/Acaricides/Nematicides abamectin, abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucytirinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenophos, promecarb, propaphos, propoxur, prothiophos, prothoate, pymetrozin, pyrachlophos, pyradaphenthion, pyresmethrin, pyrethrum, pyridaben, pyrimidifen, pyriproxifen, quinalphos,
RH 5992,
salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators is also possible.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like.

It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

When used as resistance inducers, the active compound concentrations for the treatment of parts of plants can be varied within a relatively wide range in the use forms. In general, they are between 1 and 0.0001% by weight, preferably between 0.5 and 0.001% by weight.

The preparation and the use of the substances according to the invention is illustrated by the following examples.

PREPARATION EXAMPLES

Example 1

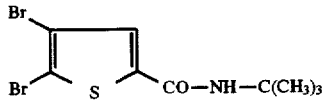

(Process a)

10 g (0.034 mol) of 4,5-dibromo-thiophene-2-carbonyl chloride in 100 ml of toluene are treated dropwise at room temperature with 5.0 g (0.068 mol) of tert-butyl-amine in 20 ml of toluene. The reaction mixture is then stirred at 50° C. for one hour, cooled to room temperature and treated with water. The organic phase is separated off, rewashed with water and concentrated under reduced pressure. After treating the residue with hexane, the crystalline residue which is deposited is filtered off and dried at 50° C. under reduced pressure. 4.8 g (41.4% of theory) of 4,5-dibromo-thiophene-2-carboxylic acid t-butyl-amide of melting point 190° C. are obtained.

Example 2

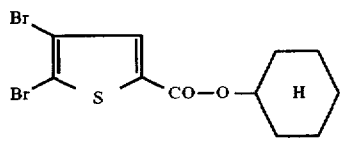

(Process b)

5 g (0.014 mol) of 4,5-dibromo-thiophene-2-carbonyl bromide in 40 ml of chloroform are treated with 1.5 g (0.015 mol) of cyclohexanol. This reaction mixture is treated dropwise with 2.1 g (0.021 mol) of triethylamine in 5 ml of chloroform and then stirred at room temperature for 2 hours.

It is then treated with water, and the organic phase is separated off, washed with water and concentrated under reduced pressure. The residue is purified by column chromatography (silica gel/methylene chloride). 4.23 g (81.1% of theory) of cyclohexyl 4,5-dibromo-thiophene-2-carboxylate of refractive index $n_D^{20}=1.5845$ are obtained.

The following dibromo-thiophene-carboxylic acid derivatives of the formula (I) are obtained correspondingly and according to the general details for preparation:

TABLE 1

(1)

| Example No. | R | Physical constant |
|---|---|---|
| 3 | —NH—OCH₂—⌬ | m.p. 109° C. |
| 4 | —NH—NH₂ | m.p. 192–194° C. |
| 5 | —O—CH₂CH₂OCH₃ | m.p. 37° C. |
| 6 | —OH | m.p. 222–224° C. |
| 7 | —NH₂ | m.p. 167–168° C. |
| 8 | —OCH₃ | m.p. 73–75° C. |
| 9 | OC₃H₇-n | $n_D^{20} = 1.5759$ |
| 10 | OC₃H₇-i | $n_D^{20} = 1.5764$ |
| 11 | —O—CH₂—⌬ | m.p. 70–72° C. |
| 12 | —O—⌬ | m.p. 113–115° C. |
| 13 | —O—CH₂—CH=CH₂ | $n_D^{20} = 1.5962$ |
| 14 | —O—CH₂—C≡CH | m.p. 54° C. |
| 15 | —O—CH(CH₃)—⌬ | $n_D^{20} = 1.5981$ |
| 16 | —O—CH(CN)—⌬ | m.p. 65° C. |
| 17 | —OC₄H₉-n | $n_D^{20} = 1.5599$ |
| 18 | —N(C₂H₅)₂ | $n_D^{20} = 1.6038$ |

TABLE 1-continued

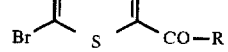

(1)

| Example No. | R | Physical constant |
|---|---|---|
| 19 | $-O-CH(CH_3)-C_4H_9\text{-}t$ | $^1$H-NMR (CDCl$_3$) $\delta$ = 0.96 ppm (3H) |
| 20 | $-O-CH_2-C_3H_7\text{-}i$ | $n_D^{20}$ = 1.5599 |
| 21 | $-O-CH(CH_3)-C\equiv CH$ | m.p. 38° C. |
| 22 | $-O-CH(CH_3)-CH=CH_2$ | $n_D^{20}$ = 1.5819 |
| 23 | $-O-CH_2CH_2-C(CH_3)=CH_2$ | $n_D^{20}$ = 1.5749 |
| 24 | 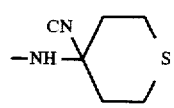 | m.p. 236–237° C. |
| 25 | $-NH-C(CH_3)(CN)$— (cyclopropyl) | m.p. 168–169° C. |
| 26 | 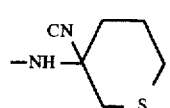 | m.p. 143–145° C. |
| 27 | 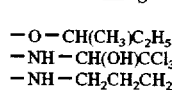 | m.p. 168–169° C. |
| 28 |  | m.p. 247–249° C. |
| 29 |  | m.p. 164–165° C. |
| 30 |  | m.p. 249–250° C. |
| 31 | (CN, NH, cyclohexyl with dioxolane) | m.p. 221–222° C. |
| 32 |  | m.p. 283–284° C. |

TABLE 1-continued (1)

| Example No. | R | Physical constant |
|---|---|---|
| 33 | CN, -NH-(thiane) | m.p. 189–191° C. |
| 34 | CN, -NH-(thiane isomer) | m.p. 202–208° C. |
| 35 | $-O-CH(CH_3)C_2H_5$ | $n_D^{20}$ = 1.5635 |
| 36 | $-NH-CH(OH)CCl_3$ | m.p. 175° C. |
| 37 | $-NH-CH_2CH_2CH_2OC_3H_7\text{-}i$ | m.p. 80° C. |
| 38 | $-NH-CH_2CH_2OH$ | m.p. 120–122° C. |
| 39 | CN, -NH-(thiolane) | m.p. 154–157° C. |

Use Examples

Example A

Pyricularia test (rice)/protective

Solvent: 12.5 parts by weight of acetone

Emulsifier: 0.3 part by weight of alkylaryl polyglycol ether

To produce a suitable preparation of active compound, 1 part by weight of active compound is mixed with the stated amounts of solvents, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

Active compounds, active compound concentrations and experimental results can be seen in the following table.

TABLE A

Pyricularia test (rice)/protective

| Active compound | Active compound concentration in % | Efficacy in % of the untreated control |
|---|---|---|
| According to the invention | | |
| Br-[thiophene, Br, Br]-C(=O)-OH (6) | 0.025 | 70 |
| Br-[thiophene, Br, Br]-C(=O)-NH₂ (7) | 0,025 | 80 |
| Br-[thiophene, Br, Br]-C(=O)-O-C₃H₇ (9) | 0.025 | 70 |
| Br-[thiophene, Br, Br]-C(=O)-O-CH₂-phenyl (11) | 0.025 | 80 |

Example B

Uncinula test (grapevine)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Unicinula necator*.

The plants are then placed in a greenhouse at 23° to 24° C. and a relative atmospheric humidity of about 75%.

Evaluation is carried out 14 days after the inoculation.

Active compounds, active compound concentrations and experimental results can be seen in the following table.

TABLE B

Uncinula test (grapevine)/protective

| Active compound | Efficacy in % of the untreated control at an active compound concentration of 25 ppm. |
|---|---|
| Br-[thiophene, Br, Br]-C(=O)-O-CH₂-phenyl (11) | 100 |

We claim:

1. A dibromo-thiophene-carboxylic acid derivative of the formula (I-A):

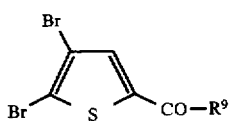

(I-A)

in which $R^9$ represents the groups —$OR^{10}$,

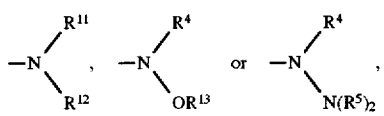

in which
$R^{10}$ represents straight-chain or branched alkyl having 1 to 12 carbon atoms, which is mono- to pentasubstituted, identically or differently, by halogen or alkoxy having 1 to 6 carbon atoms; or
represents straight-chain or branched alkenyl having 3 to 6 carbon atoms; or
represents cycloalkyl having 3 to 7 carbon atoms or cycloalkylalkyl having 3 to 7 carbon atoms in the cycloalkyl moiety and 1 to 4 carbon atoms in the straight-chain or branched alkyl moiety; or
represents aryl having 6 to 10 carbon atoms or aralkyl having 6 to 10 carbon atoms in the aryl moiety and 1 to 4 carbon atoms in the straight-chain or branched alkyl moiety, which alkyl moiety is optionally substituted by cyano, and wherein each of the aryl moieties is optionally mono- to trisubstituted, identically or differently, by halogen, hydroxyl, cyano, nitro, alkyl, alkoxy or alkylthio, each of which is straight-chain or branched and has 1 to 4 carbon atoms, cycloalkyl having 3 to 7 carbon atoms, halogenoalkyl, halogenoalkoxy or halogenoalkylthio, each of which is straight-chain or branched, has 1 to 4 carbon atoms, and 1 to 5 identical or different halogen atoms, or phenyl, which is optionally mono- to trisubstituted, identically or differently, by halogen or alkyl having 1 to 4 carbon atoms;

$R^{11}$ represents hydrogen or straight-chain or branched alkyl having 1 to 12 carbon atoms;

$R^{12}$ represents straight-chain or branched alkyl having 1 to 12 carbon atoms, which is mono- to pentasubstituted, identically or differently, by halogen, cyano, amino, hydroxyl, mercapto, nitro, straight-chain or branched alkoxy having 1 to 6 carbon atoms, or straight-chain or branched alkylthio having 1 to 6 carbon atoms; or
represents cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which alkyl moiety is optionally substituted by cyano, and wherein each of the cycloalkyl moieties is optionally mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, or cycloalkyl having 3 to 7 carbon atoms, which is optionally mono- to trisubstituted, identically or differently, by alkyl having 1 to 4 carbon atoms and/or by phenyl, which phenyl is optionally mono- to trisubstituted, identically or differently, by straight-chain or branched alkyl having 1 to 4 carbon atoms, halogen, or straight-chain or branched halogenoalkyl having 1 to 4 carbon atoms and 1 to 5 identical or different halogen atoms; or
represents tetrahydrothiophene or tetrahydropyran, each of which is optionally mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, or cycloalkyl having 3 to 7 carbon atoms, which is optionally mono- to trisubstituted, identically or differently, by alkyl having 1 to 4 carbon atoms and/or by phenyl, which phenyl is optionally mono- to trisubstituted, identically or differently, by straight-chain or branched alkyl having 1 to 4 carbon atoms, halogen, or straight-chain or branched halogenoalkyl having 1 to 4 carbon atoms and 1 to 5 identical or different halogen atoms; or
represents aralkoxy having 6 or 10 carbon atoms in the aryl moiety and 1 to 4 carbon atoms in the straight-chain or branched alkoxy moiety, which alkoxy moiety is optionally substituted by cyano, and wherein the aryl moiety is optionally mono- to trisubstituted, identically or differently, by halogen, hydroxyl, cyano, nitro, alkyl, alkoxy or alkylthio, each of which is straight-chain or branched and has 1 to 4 carbon atoms, cycloalkyl having 3 to 7 carbon atoms, halogenoalkyl, halogenoalkoxy or halogenoalkylthio, each of which is straight-chain or branched, has 1 to 4 carbon atoms, and 1 to 5 identical or different halogen atoms, or phenyl, which is optionally mono- to trisubstituted, identically or differently, by halogen or alkyl having 1 to 4 carbon atoms;

$R^4$ and $R^5$ are identical or different and represent straight-chain or branched alkyl having 1 to 12 carbon atoms, which is mono- to pentasubstituted, identically or differently, by halogen, cyano, amino, hydroxyl, mercapto, carboxyl, nitro, alkoxy, alkylthio or alkoxycarbonyl, each of which is straight-chain or branched and has 1 to 6 carbon atoms in the individual alkyl moieties, —$NR^7R^8$, or straight-chain or branched alkenyl or alkynyl, each of which has 3 to 6 carbon atoms and is optionally mono- to pentasubstituted by identical or different halogen;

$R^7$ represents straight-chain or branched alkyl having 1 to 6 carbon atoms, which is optionally mono- to pentasubstituted, identically or differently, by halogen, cyano, amino, hydroxyl, mercapto, nitro, carboxyl, alkoxy or alkoxycarbonyl, each of which is straight-chain or branched and has 1 to 6 carbon atoms in the alkoxy moieties, or alkylamino or dialkylamino, each of which has 1 to 6 carbon atoms in each straight-chain or branched alkyl moiety; or
represents straight-chain or branched alkenyl or alkynyl, each having 3 to 6 carbon atoms and being optionally substituted by 1 to 5 identical or different halogen atoms; or
represents benzyl, which is optionally mono- to trisubstituted on the phenyl moiety, identically or differently, by halogen, nitro, cyano, straight-chain or branched alkyl having 1 to 6 carbon atoms, or halogenoalkyl, halogenoalkoxy, or halogenoalkylthio, each of which is straight-chain or branched, has 1 to 4 carbon atoms, and 1 to 5 identical or different halogen atoms;

$R^8$ represents hydrogen, or straight-chain or branched alkyl having 1 to 6 carbon atoms, which is optionally mono- to pentasubstituted, identically or differently, by halogen, cyano, amino, hydroxyl, mercapto, nitro, carboxyl, alkoxy or alkoxycarbonyl, each of which is straight-chain or branched and has 1 to 6 carbon atoms in the alkoxy moieties, or alkylamino or dialkylamino, each of which has 1 to 6 carbon atoms in each straight-chain or branched alkyl moiety; or represents straight-chain or branched alkenyl or alkynyl, each having 3 to 6 carbon atoms and being optionally substituted by 1 to 5 identical or different halogen atoms; or represents benzyl, which is optionally mono- to trisubstituted on the phenyl moiety, identically or differently, by halogen, nitro, cyano, straight-chain or branched alkyl having 1 to 6 carbon atoms, or halogenoalkyl, halogenoalkoxy, or halogenoalkylthio, each of which is straight-chain or branched, has 1 to 4 carbon atoms, and 1 to 5 identical or different halogen atoms; or $R^7$ and $R^8$ together represent divalent alkanediyl having 4 to 6 methylene groups, it being possible for a methylene group to be replaced by O, S or $NR^6$, wherein $R^6$ represents hydrogen, or alkyl or alkoxycarbonyl, each of which is straight-chain or branched and has 1 to 6 carbon atoms in the alkyl moieties; and $R^{13}$ represents hydrogen or straight-chain or branched alkyl having 1 to 12 carbon atoms, which alkyl is mono- to pentasubstituted, identically or differently, by halogen, cyano, amino, hydroxyl, mercapto, carboxyl, nitro, or alkoxy, alkylthio or alkoxycarbonyl, each of which is straight-chain or branched and has 1 to 6 carbon atoms in the individual alkyl moieties.

2. A method of controlling undesired microorganisms, which method comprises applying to such undesired microorganisms or to their habitat a microbicidally effective amount of a dibromo-thiophene-carboxylic acid derivative of the formula

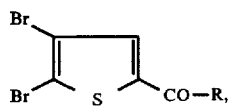

in which

R represents the groups —$XR^1$, —$NR^2R^3$, —$NR^4OR^5$ and —$NR^4$—$N(R^5)_2$, X represents oxygen or sulphur, $R^1$ represents hydrogen, or straight-chain or branched alkyl having 1 to 12 carbon atoms, which can be mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or represents straight-chain or branched alkenyl and alkinyl having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned can be mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms which is optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals is optionally mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, which is optionally mono- to trisubstituted, identically or differently, by alkyl having 1 to 4 carbon atoms, and/or by phenyl, which for its part is optionally mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aryl having 6 to 10 carbon atoms or aralkyl having 6 to 10 carbon atoms in the aryl moiety and 1 to 4 carbon atoms in the straight-chain or branched alkyl moiety, which is optionally substituted by cyano, where each of the two radicals in the aryl moiety can be mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl which for its part is optionally mono- to trisubstituted, identically or differently, by halogen and/or alkyl having 1 to 4 carbon atoms, or 5- or 6-membered hetaryl or 5- or 6-membered hetarylalkyl having 1 to 6 carbon atoms in the straight-chain or branched alkyl moiety, which is optionally substituted by cyano, where the hetaryl moiety in each case contains 1 to 3 heteroatoms, selected from the group consisting of oxygen, sulphur and nitrogen, and which is optionally mono- to trisubstituted, identically or differently, by straight chain or branched alkyl having 1 to 6 carbon atoms, halogen, cyano and/or straight-chain or branched halogenoalkyl having 1 to 4 carbon atoms and 1 to 5 identical or different halogen atoms, $R^2$ and $R^3$ are identical or different and represent hydrogen, or straight-chain or branched alkyl having 1 to 12 carbon atoms, which can be mono- to pentasubstituted, identically or differently, by halogen, cyano, amino, hydroxyl, mercapto, nitro, straight-chain or branched alkoxy having 1 to 6 carbon atoms, straight-chain or branched alkylthio having 1 to 6 carbon atoms and/or the group

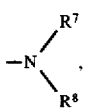

or straight-chain or branched alkenyl or alkinyl having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned are optionally mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part is optionally mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals is optionally mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part is optionally mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aralkoxy having 6 or 10 carbon atoms in the aryl moiety and 1 to 4 carbon atoms in the straight-chain or branched alkoxy moiety, optionally substituted by cyano, where the aryl moiety is optionally mono- to trisubstituted, identically or differently, by halogen, hydroxyl, cyano, nitro; alkyl, alkoxy or alkylthio, each of which is straight-chain or branched each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl, which for its part is optionally mono- to trisubstituted, identically or differently, by halogen and/or alkyl having 1 to 4 carbon atoms, $R^3$ additionally represents 5- or 6-membered hetaryl or 5- or 6-membered hetarylalkyl having 1 to 6 carbon atoms in the straight-chain or branched alkyl moiety, optionally substituted by cyano, where the hetaryl moiety in each case contains 1 to 3 heteroatoms and is optionally mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms, $R^2$ and $R^3$ additionally together represent divalent alkanediyl having 2 to 6 $CH_2$ groups, where a $CH_2$ group is optionally replaced by O, S or $NR^6$, $R^4$ and $R^5$ are identical or different and represent hydrogen, or straight-chain or branched alkyl having 1 to 12 carbon atoms, which is optionally mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or straight-chain or branched alkenyl and alkinyl having 3 to 6 carbon atoms, each of which is optionally mono- to pentasubstituted, identically or differently, by halogen, or aralkyl having 6 or 10 carbon atoms in the aryl moiety and 1 to 4 carbon atoms in the straight-chain or branched alkyl moiety, optionally substituted by cyano, where the aryl moiety is optionally mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl, which for its part is optionally mono- to trisubstituted, identically or differently, by halogen and/or alkyl having 1 to 4 carbon atoms, $R^6$ represents hydrogen and also alkyl and alkylcarbonyl, each of which is straight-chain or branched, each having 1 to 6 carbon atoms in the alkyl moiety, $R^7$ represents straight-chain or branched alkyl having 1 to 6 carbon atoms, which is optionally mono- to pentasubstituted, identically or differently, by halogen, cyano, amino, hydroxyl, mercapto, nitro, carboxyl; alkoxy and alkoxycarbonyl, each of which is straight-chain or branched, each having 1 to 6 carbon atoms in the alkoxy moieties; alkylamino and dialkylamino having 1 to 6 carbon atoms in each straight-chain or branched alkyl moiety, or straight-chain or branched alkenyl or alkinyl each having 3 to 6 carbon atoms, each of which is optionally substituted by 1 to 5 identical or different halogen atoms, or benzyl which in the phenyl moiety is optionally mono- to trisubstituted, identically or differently, by halogen, nitro, cyano, straight-chain or branched alkyl having 1 to 6 carbon atoms, and also halogenoalkyl, halogenoalkoxy or halogenoalkylthio, each of which is straight-chain or branched, each having 1 to 4 carbon atoms and 1 to 5 identical or different halogen atoms and $R^8$ represents hydrogen, or straight-chain or branched alkyl having 1 to 6 carbon atoms, which is optionally mono- to pentasubstituted, identically or differently, by halogen, cyano, amino, hydroxyl, mercapto, nitro, carboxyl; alkoxy and alkoxycarbonyl, each of which is straight-chain or branched, each having 1 to 6 carbon atoms in the alkoxy moieties, alkylamino and dialkylamino having 1 to 6 carbon atoms in each straight-chain or branched alkyl moiety, or straight-chain or branched alkenyl or alkinyl each having 3 to 6 carbon atoms, each of which is optionally substituted by 1 to 5 identical or different halogen atoms, or benzyl which in the phenyl moiety is optionally mono- to trisubstituted, identically or differently, by halogen, nitro, cyano, straight-chain or branched alkyl having 1 to 6 carbon atoms, and also halogenoalkyl, halogenoalkoxy or halogenoalkylthio, each of which is straight-chain or branched, each having 1 to 4 carbon atoms and 1 to 5 identical or different halogen atoms, or $R^7$ and $R^8$ additionally together represent divalent alkanediyl having 4 to 6 $CH_2$ groups, it optionally being possible for a $CH_2$ group to be replaced by O, S or $NR^6$ and $R^6$ having the meanings mentioned above.

3. The method as claimed in claim 2, wherein the microbicidally active compound is the dibromo-thiophene-carboxylic acid derivative of the formula

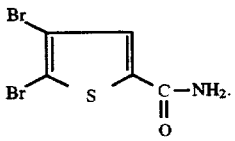

4. The method as claimed in claim 2, wherein the microbicidally active compound is the dibromo-thiophene-carboxylic acid derivative of the formula

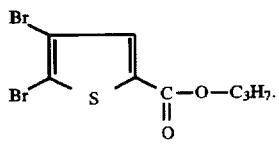

5. The method as claimed in claim 2, wherein the microbicidally active compound is the dibromo-thiophene-carboxylic acid derivative of the formula

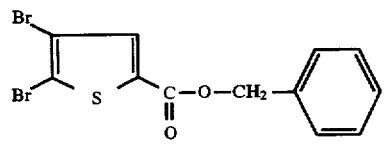

6. A dibromo-thiophene-carboxylic acid derivative of the formula

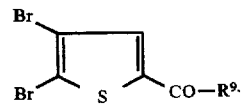

(I-A)

in which $R^9$ represents the groups —$OR^{10}$,

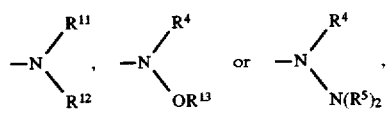

$R^{10}$ represents straight-chain or branched alkyl having 1 to 12 carbon atoms, which is mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or represents straight-chain or branched alkenyl having 3 to 6 carbon atoms, which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned can be mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms which is optionally mono- to trisubstituted, identically or differently, by alkyl having 1 to 4 carbon atoms, and/or by phenyl, which for its part is optionally mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals is optionally mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, which is optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aryl having 6 to 10 carbon atoms or aralkyl having 6 to 10 carbon atoms in the aryl moiety and 1 to 4 carbon atoms in the straight-chain or branched alkyl moiety, which is optionally substituted by cyano, where each of the two radicals in the aryl moiety is optionally mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl which for its part can be mono- to trisubstituted, identically or differently, by halogen and/or alkyl having 1 to 4 carbon atoms, or 5- or 6-membered hetaryl or 5- or 6-membered hetarylalkyl having 1 to 6 carbon atoms in the straight-chain or branched alkyl moiety, which is optionally substituted by cyano, where the hetaryl moiety in each case contains 1 to 3 heteroatoms selected from the group consisting of oxygen, sulphur and nitrogen, and which is optionally mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms, $R^{11}$ and $R^{12}$ are identical or different and represent straight-chain or branched alkyl having 1 to 12 carbon atoms, which is mono- to pentasubstituted, identically or differently, by halogen, cyano, amino, hydroxyl, mercapto, nitro, straight-chain or branched alkoxy having 1 to 6 carbon atoms, straight-chain or branched alkylthio having 1 to 6 carbon atoms and/or the group

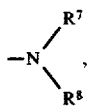

or straight-chain or branched alkenyl or alkinyl having 3 to 6 carbon atoms, each of which is optionally mono- to pentasubstituted, identically or differently, by halogen, or cycloalkyl having 3 to 7 carbon atoms or cycloalkylalkyl having 3 to 7 carbon atoms in the cycloalkyl moiety and 1 to 4 carbon atoms in the straight-chain or branched alkyl moiety, which is optionally substituted by cyano, where the cycloalkyl moiety of the two radicals mentioned are optionally mono- to pentasubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part is optionally mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or tetrahydrofuran, tetrahydrothiophene, tetrahydropyran or tetrahydrothiopyran, where each of these radicals is optionally mono- to trisubstituted, identically or differently, by straight-chain or branched alkyl having 1 to 4 carbon atoms, halogen, straight-chain or branched halogenoalkyl having 1 to 4 carbon atoms and 1 to 5 identical or different halogen atoms, cyano, alkylenedioxo having 1 to 3 carbon atoms, cycloalkyl having 3 to 7 carbon atoms, optionally mono- to trisubstituted, identically or differently, by alkyl having 1 to 4 carbon atoms, and/or by phenyl, which for its part can be mono- to trisubstituted, identically or differently, by straight-chain or branched alkyl having 1 to 4 carbon atoms, halogen and straight-chain or branched halogenoalkyl having 1 to 4 carbon atoms and 1 to 5 identical or different halogen atoms, or aralkoxy having 6 or 10 carbon atoms in the aryl moiety and 1 to 4 carbon atoms in the straight-chain or branched alkoxy moiety, optionally substituted by cyano, where the aryl moiety is optionally mono- to trisubstituted, identically or differently, by halogen, hydroxyl, cyano, nitro; alkyl, alkoxy or alkylthio, each of which is straight-chain or branched each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl, which for its part can be mono- to trisubstituted, identically or differently, by halogen and/or alkyl having 1 to 4 carbon atoms, $R^{12}$ additionally represents 5- or 6-membered hetaryl optionally substituted by cyano, where the hetaryl moiety in each case contains 1 to 3 heteroatoms and is optionally mono- to trisubstituted, identically or differently, by straight-chain or branched alkyl having 1 to 6 carbon atoms, halogen, cyano and/or straight-chain or branched halogenoalkyl having 1 to 4 carbon atoms and 1 to 5 identical or different halogen atoms, or $R^{11}$ and $R^{12}$ together represent divalent alkanediyl having 2 to 6 $CH_2$ groups, where a $CH_2$ group is optionally replaced by O, S or $NR^6$, $R^4$ and $R^5$ are identical or different and represent straight-chain or branched alkyl having 1 to 12 carbon atoms, which is mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or straight-chain or branched alkenyl and alkinyl having 3 to 6 carbon atoms, each of which is optionally mono- to pentasubstituted, identically or differently, by halogen, $R^6$ represents hydrogen and also alkyl and alkylcarbonyl, each of which is straight-chain or branched, each having 1 to 6 carbon atoms in the alkyl moiety;

$R^7$ represents straight-chain or branched alkyl having 1 to 6 carbon atoms, which is optionally mono- to pentasubstituted, identically or differently, by halogen, cyano, amino, hydroxyl, mercapto, nitro, carboxyl; alkoxy and alkoxycarbonyl, each of which is straight-chain or branched, each having 1 to 6 carbon atoms in the alkoxy moieties; alkylamino and dialkylamino having 1 to 6 carbon atoms in each straight-chain or branched alkyl moiety, or straight-chain or branched alkenyl or alkinyl each having 3 to 6 carbon atoms, each of which is optionally substituted by 1 to 5 identical or different halogen atoms, or benzyl which in the phenyl moiety is optionally mono- to trisubstituted identically or differently, by halogen, nitro, cyano, straight-chain or branched alkyl having 1 to 6 carbon atoms, and also halogenoalkyl, halogenoalkoxy or halogenoalkylthio, each of which is straight-chain or branched, each having 1 to 4 carbon atoms and 1 to 5 identical or different halogen atoms and $R^8$ represents hydrogen, or straight-chain or branched alkyl having 1 to 6 carbon atoms, which is optionally mono- to pentasubstituted, identically or differently, by halogen, cyano, amino, hydroxyl, mercapto, nitro, carboxyl; alkoxy and alkoxycarbonyl, each of which is straight-chain or branched, each having 1 to 6 carbon atoms in the alkoxy moieties, alkylamino and dialkylamino having 1 to 6 carbon atoms in each straight-chain or branched alkyl moiety, or straight-chain or branched alkenyl or alkinyl each having 3 to 6 carbon atoms, each of which is optionally substituted by 1 to 5 identical or different halogen atoms, or benzyl which in the phenyl moiety is optionally mono- to trisubstituted, identically or differently, by halogen, nitro, cyano, straight-chain or branched alkyl having 1 to 6 carbon atoms, and also halogenoalkyl, halogenoalkoxy or halogenoalkylthio, each of which is straight-chain or branched, each having 1 to 4 carbon atoms and 1 to 5 identical or different halogen atoms, or $R^7$ and $R^8$ additionally together represent divalent alkanediyl having 4 to 6 $CH_2$ groups, it optionally being possible for a $CH_2$ group to be replaced by O, S or $NR^6$ and $R^6$ having the meanings mentioned above, and $R^{13}$ represents hydrogen, or straight-chain or branched alkyl having 1 to 12 carbon atoms, which is mono- to pentasubstituted, identically or differently, by halogen, cyano, amino, hydroxyl, mercapto, carboxyl, nitro; alkoxy, alkylthio or alkoxycarbonyl, each of which is straight-chain or branched, each having 1 to 6 carbon atoms in the individual alkyl moieties; and also the group —$NR^7R^8$, or straight-chain or branched alkenyl and alkinyl having 3 to 6 carbon atoms, each of which is optionally mono- to pentasubstituted, identically or differently, by halogen, or aralkyl having 6 or 10 carbon atoms in the aryl moiety and 1 to 4 carbon atoms in the straight-chain or branched alkyl moiety, optionally substituted by cyano, where the aryl moiety is optionally mono- to trisubstituted, identically or differently, by halogen, hydroxyl, cyano, nitro; alkyl, alkoxy or alkylthio, each of which is straight-chain or branched, each having 1 to 4 carbon atoms; cycloalkyl having 3 to 7 carbon atoms; halogenoalkyl, halogenoalkoxy or halogenoalkylthio, each of which is straight-chain or branched, each having 1 to 4 carbon atoms and 1 to 5 identical or different halogen atoms; and/or by phenyl, which for its part is optionally mono- to trisubstituted, identically or differently, by halogen and/or alkyl having 1 to 4 carbon atoms.

7. A microbicidal composition comprising a microbicidally effective amount of a compound as claimed in claim 1 and an inert diluent.

* * * * *